(12) United States Patent
Erben et al.

(10) Patent No.: US 8,309,037 B2
(45) Date of Patent: Nov. 13, 2012

(54) METHOD AND APPARATUS FOR PROCESSING TISSUE SAMPLES USING A SENSOR

(75) Inventors: Michael Erben, Oberhausen-Rheinhausen (DE); Nils Jakob, Nussloch (DE); Claus Haberkorn, Dielheim (DE); Frank Meder, Bammental (DE); Michael Rapp, Oftersheim (DE); Joachim Hoffmann, Lorsch (DE)

(73) Assignee: Leica Biosystems Nussloch GmbH, Nussloch (DE)

( * ) Notice: Subject to any disclaimer, the term of this patent is extended or adjusted under 35 U.S.C. 154(b) by 496 days.

(21) Appl. No.: 12/606,964

(22) Filed: Oct. 27, 2009

(65) Prior Publication Data

US 2010/0112625 A1   May 6, 2010

(30) Foreign Application Priority Data

Oct. 31, 2008   (DE) .......................... 10 2008 054 066

(51) Int. Cl.
*A61B 10/00* (2006.01)

(52) U.S. Cl. .......... 422/536; 422/537; 422/547; 422/50; 435/3; 435/40.5; 436/180

(58) Field of Classification Search ............... 422/50, 422/536–537, 547; 435/3, 40.5; 436/180
See application file for complete search history.

(56) References Cited

FOREIGN PATENT DOCUMENTS

| DE | 196 81 647 | 12/1998 |
|---|---|---|
| EP | 1 793 218 | 6/2007 |
| WO | 97/19379 | 5/1997 |
| WO | 2004059288 | 7/2004 |
| WO | 2005031312 | 4/2005 |

*Primary Examiner* — Jyoti Nagpaul
(74) *Attorney, Agent, or Firm* — Schlee IP International, P.C.; Alexander R. Schlee

(57) ABSTRACT

An apparatus and a method for processing tissue samples are described. The apparatus comprises: at least one retort for accommodating tissue samples; at least one container for storing alcohol or xylene; a valve adapted to connect the at least one retort with the at least one container depending on an operating position of the valve; and at least a first sensor that is arranged in flow direction between the container and the retort for measuring a value of a parameter that represents a purity level of the alcohol or xylene; wherein the first sensor and the valve are configured to replace the alcohol or xylene depending on the value of the parameter that represents the purity level. The method comprises for the alcohol or xylene conducting between the container and the retort; automatically measuring the purity level and replacing depending on the purity level.

10 Claims, 4 Drawing Sheets

METHOD AND APPARATUS FOR PROCESSING TISSUE SAMPLES USING A SENSOR

CROSS-REFERENCE TO RELATED APPLICATION

This application claims the priority of the German patent application DE 102008054066.8 having a filing date of Oct. 31, 2008. The entire content of this prior application DE 102008054066.8 is herewith incorporated by reference.

BACKGROUND OF THE INVENTION

The invention relates to an apparatus and a method for processing tissue samples. The apparatus comprises at least one retort for accommodating the tissue samples and at least one container for storing a process medium. The container communicates with the retort depending on an operating position of a valve.

Biological tissue samples, in particular histological tissue samples, are often needed in the field of human medicine and veterinary medicine, in particular as a microscopic preparation for the assessment of cells and their surroundings. For the microscopic examination, thin sections of the tissue sample have to be prepared, which are assessed by an expert in incident light or in transmitted light under the microscope.

For preparing thin sections, for example with the aid of a microtome, the tissue sample must have a certain solidity so that thin transparent sections having a thickness in the micrometer range can be prepared with the aid of a knife. To this end, the tissue sample first has to go through a treatment process in which it is fixed, dehydrated, cleared and then infiltrated with a carrier material, preferably molten paraffin. Often, these processes are successively performed in one single apparatus, the so-called tissue processor, which, to this end, includes a closable process chamber, called retort, which accommodates the different reagents for performing the process steps at a suitable temperature and pressure.

An important process step in this connection is the infiltration of the tissue sample with the carrier material in order to stabilize and solidify the tissue sample. Prior to this infiltration process step, the clearing step is performed in which alcohol residuals still present from the dehydration step are removed. As a chemical solution for this clearing step xylene or a similar agent is used. In the subsequent infiltration step, in which the tissue sample is exposed to the carrier material, usually molten paraffin, still remaining xylene components are flushed out and absorbed by the liquid carrier material, as a result whereof the carrier material is contaminated in the retort. In the same way, residual dehydrating reagents are removed in the clearing step. Constituents dissolved out of the tissue sample itself can likewise contaminate the dehydrating reagents, the clearing reagents or the carrier material. Therefore, it is necessary that the individual process steps are divided into several partial process steps, in which the tissue sample is successively exposed to different reagents with increasing purity level within the use of one reagent.

When, for example, the infiltration process is divided into three process steps, then the tissue sample is first treated with a first carrier material which may have a relatively high contamination degree, for example, contaminated with xylene. Thereafter, a second infiltration step with a second carrier material is performed which has a higher purity level than the first carrier material. Finally, the tissue sample is exposed to a third carrier material having the highest purity level, wherein the carrier materials may comprise xylene or further reagents. In this way, the tissue sample is completely infiltrated with carrier material in a step-wise process with increasing purity level of the carrier material used for the treatment, the carrier material having sufficiently high quality for preparing a good thin section in a microtome and for a microscopic preparation.

The use of several liquid reagents with different purity levels makes it necessary that these reagents are kept ready in containers in a liquid state. When one of the reagents is contaminated too much, mostly this applies to the mentioned first reagent, then this reagent has to be replaced by a reagent having an improved purity level.

SUMMARY OF THE INVENTION

It is the object of the invention to specify a method and an apparatus for processing tissue samples, which easily contribute to a high quality of the finished tissue samples.

This object is achieved by an apparatus for processing tissue samples, comprising: at least one retort for accommodating tissue samples; at least one container for storing alcohol or xylene; a valve adapted to connect the at least one retort with the at least one container depending on an operating position of the valve; and at least a first sensor that is arranged in flow direction between the container and the retort for measuring a measured value of a parameter that represents a purity level of the alcohol or xylene; wherein the first sensor and the valve are configured to replace the alcohol or xylene depending on the measured value of the parameter that represents the purity level.

This object is further achieved by a method for processing tissue samples with the aforementioned apparatus, the method comprising: conducting alcohol or xylene at least one of from the container into the retort and from the retort into the container; automatically measuring by means of the sensor a measured value of a parameter that represents the purity level of the alcohol or xylene; and replacing the alcohol or xylene depending on the measured value of the parameter that represents the purity level.

According to the invention an apparatus for processing tissue samples comprises at least one retort for accommodating the tissue samples and at least one container for storing a process medium. The container communicates with the retort depending on an operating position of a valve. At least one sensor is provided which is arranged between the container and the retort in flow direction. The sensor is provided for detecting a measured value of a measured quantity which is representative of a purity level of the process medium.

The flow direction refers to the direction in which the process medium flows. In particular, this can be from the container to the retort or from the retort back to the container. The sensor easily enables to automatically detect whether the purity level of the process medium meets a predetermined condition. This allows to easily recognize when the process medium either has to be replaced for performing a predetermined process step or has to be used for another process step and thus has to be re-classified. The process medium can, for example, be a fixation reagent, a dehydrating reagent, an intermedium, a carrier material or a cleaning reagent.

DETAILED DESCRIPTION OF THE INVENTION

Preferably, the sensor is arranged in flow direction between the retort and the valve. This is particularly advantageous when several containers with different process media are provided, and the process media are all controlled via the same valve.

The arrangement of the sensor between the valve and the retort then enables to detect the purity level of different process media with one single sensor. In this connection actually chemically identical reagents with merely different purity levels or chemically totally different process reagents are referred to as different process media.

If the process media are so different from one another that different sensors are required for checking their purity levels, then a sensor module can be provided which comprises at least the one sensor and respective further sensors. Preferably, the further sensors are then arranged according to the one sensor.

During the processing of the tissue sample in the retort, the process medium or the process media are regularly transported, in particular pumped, from the respective containers to the retort and back again. While doing so, they are guided past the sensor such that it enables the determination of the purity level. The purity control can be performed during pumping of the process medium to the retort as well as to the respective container. Preferably, it is automatically decided depending on the determined purity level whether the respective process medium is to be replaced or successively used for other process steps than the present process step.

BRIEF DESCRIPTION OF THE DRAWINGS

Embodiments of the invention are explained in the following with reference to the enclosed drawings.

DETAILED DESCRIPTION OF THE DRAWINGS

Identical parts in the various figures are identified by identical reference signs.

Figure 1:
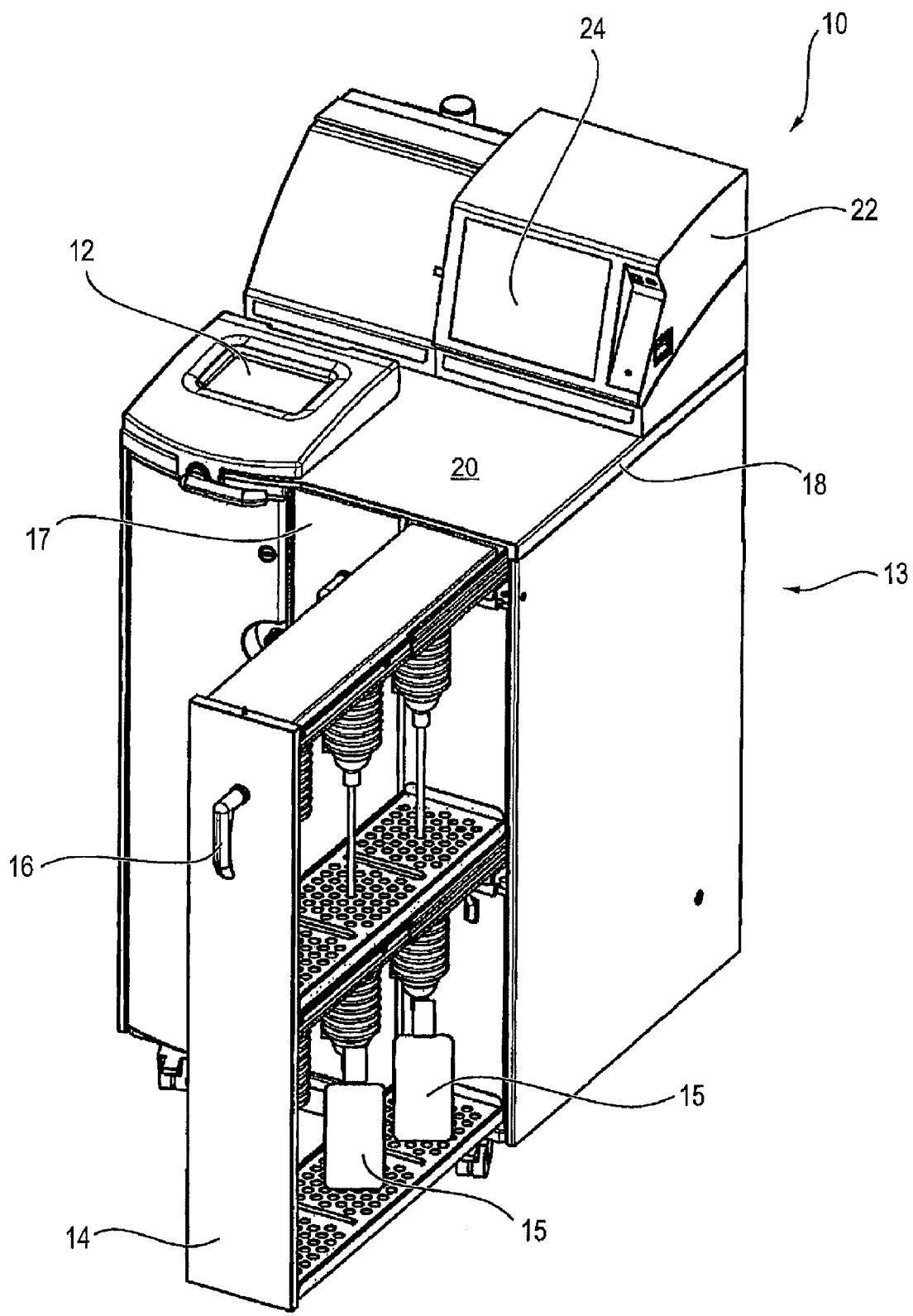
FIG. 1 shows a tissue processor.
Figure 4:
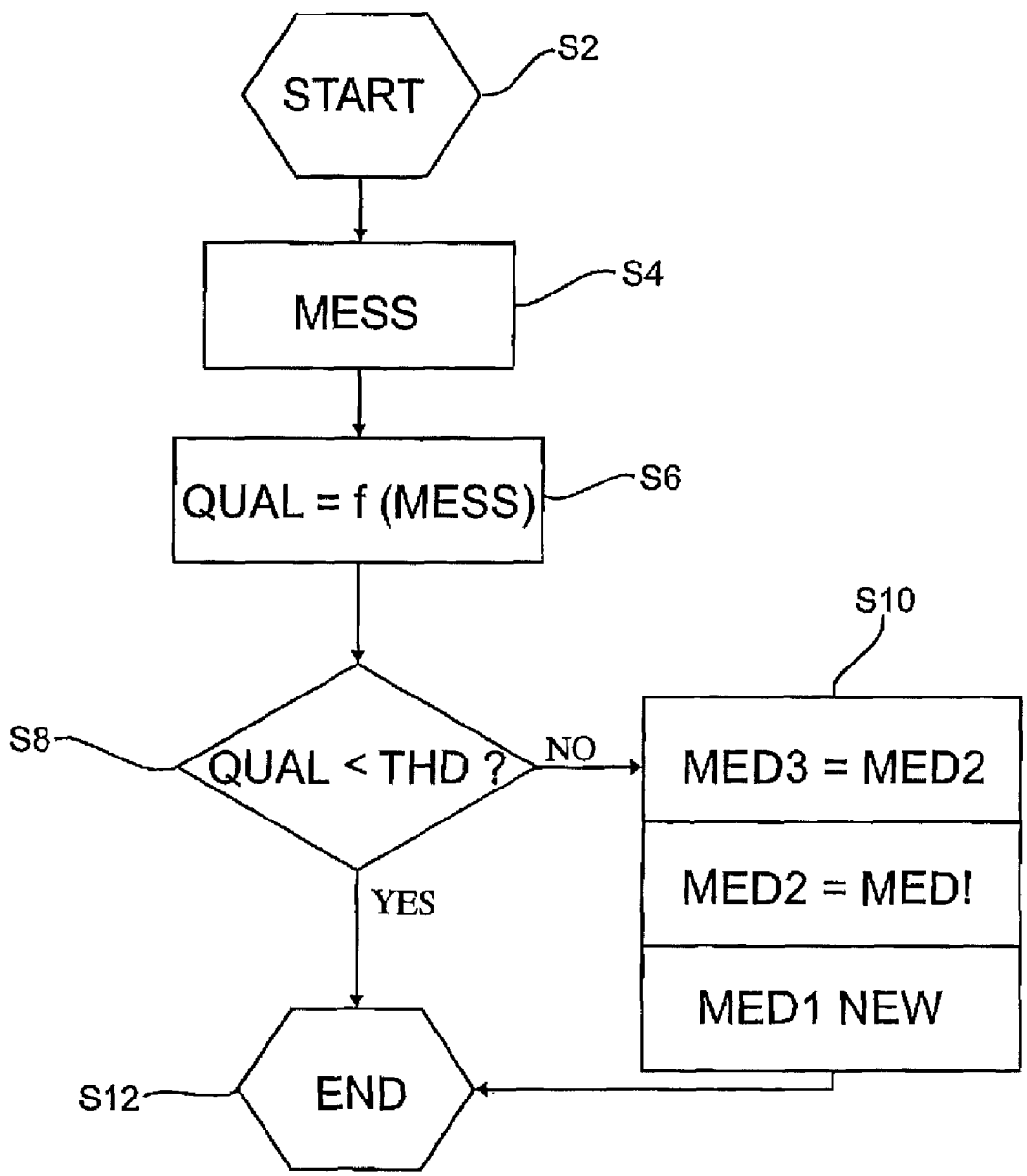
FIG. 4 shows a flow chart of a program for operating the tissue processor.

FIG. 1 schematically shows a tissue processor 10, with which the method according to the invention can be performed. In this connection, the tissue processor 10 can also be referred to as an apparatus for processing tissue samples. The tissue processor 10 comprises a retort 12 for processing tissue samples with different reagents. In this retort 12, the tissue samples go through several process steps, in particular a fixation process, in which formalin is typically used. Thereafter, a dehydration process is performed with alcohol solutions of different purity levels QUAL (FIG. 4). In a subsequent clearing process, alcohol residuals are removed from the tissue samples and the tissue samples are prepared for the uptake of carrier material. In this clearing process, xylene or a similar agent is often used. As a carrier material, preferably paraffin or wax in different compositions is used. The process steps can be divided into several partial process steps, within which the tissue samples are, for example, exposed to the mentioned reagents with increasing purity level QUAL (FIG. 4).

After going through these process steps, a cleaning process can be performed with the mentioned or with further reagents, for example, by execution of the mentioned process steps the other way around without tissue samples.

The tissue processor 10 comprises a cabinet 13 with drawers. A drawer 14 serves for accommodating reagents 15 (only two of a large number are shown), which are necessary so that the fixation process, the dehydration process and/or the clearing process can be performed. The drawer 14 has a handle 16 for operation. A further drawer 17 (only partially shown) contains components for the infiltration process described below.

On a table plate 18 a working area 20 is provided. Further, on the table plate 18, a control device 22 with a screen 24 is arranged. The control device 22 controls the treatment processes for the tissue samples with the aid of a computer.

Figure 2:
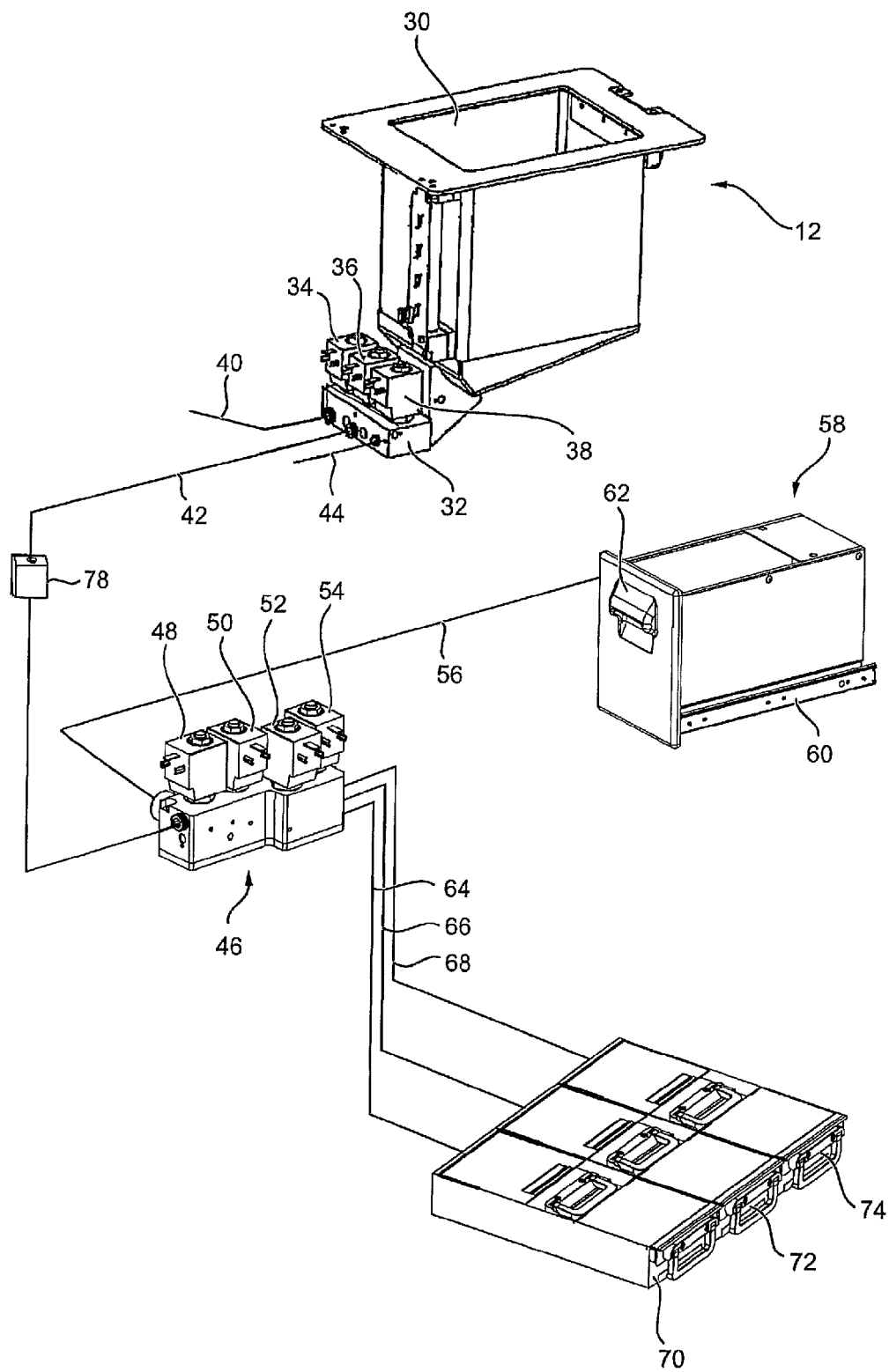
FIG. 2 shows various components of a tissue processor relating to the infiltration of tissue samples with paraffin.

FIG. 2 shows important components for performing the process for the infiltration of tissue samples with carrier material, in particular paraffin or wax.

The retort 12 is formed as a lockable chamber having an opening 30 which can be closed. Within the retort 12, different reagents, in particular the paraffin which is important for the infiltration process, can be subjected to pressure, vacuum and temperature. The interior of the retort 12 is connected via a valve arrangement 32 to conduits 40, 42, 44 via electrically controllable valves 34, 36 or 38, respectively.

The conduit 42 is connected to the content of the retort 12 via the valve 36. Controlled via the valve 36, liquid paraffin is supplied and discharged via the conduit 42. A further conduit 44 serves for the connection to further reagents for the fixation process, the dehydration process and/or the clearing process, which will be described further below.

The conduit 42 is connected to a distributor 46 which, controlled via valves 48, 50, 52, 54, distributes liquid paraffin. Connected to the distributor 46 is the conduit 56 which connects it to a supply station 58 for paraffin. The supply station 58 is formed as a drawer and comprises pull-out rails 60 and a handle 62.

Further, three conduits 64, 66, 68 are connected to the distributor 46 for connecting it to a first container 70, a second container 72 or a third container 74, respectively. These containers 70, 72, 74 contain liquid paraffin with increasing purity level QUAL. The containers 70, 72, 74, too, are formed as drawers and can be pulled out of the chamber of the tissue processor 12 and subsequently be removed.

All conduits 40, 42, 56, 64, 66, 68 are heated, as is the distributor 46 and, depending on the reagent used, also the valve arrangement 32 to ensure that the paraffin is always kept in a liquid state, for example, at 65° C., and does not solidify in operation.

The same applies to the retort 12 and its component parts as well as to the supply station 58 and the containers 70, 72, 74. The respective heating elements are omitted in the Figure for clarity reasons.

The supply station 58 has a considerably larger volume than the respective container 70, 72, 74. It also serves to melt paraffin which is present in the solid state as paraffin pellets or paraffin scales. The bulk volume of paraffin pellets or paraffin scales is considerably larger than the liquid volume of molten paraffin for the same weight. The larger volume of the supply station 58 thus allows that sufficient bulk volume of solid paraffin can be filled in, without solid paraffin having to be refilled for a sufficient liquid supply. In this way, the handling with solid paraffin is facilitated. Moreover, the liquid volume of the supply station 58 is sufficiently large so that it can supply the containers 70, 72, 74 with uncontaminated paraffin for a relatively long operating time, for example also in the case of an automatic operation during nighttime, when operating personnel does not have to be present.

Between the containers 70, 72, 74 and the retort 12, in particular between the distributor 46 with its valves 48, 50, 52, 54, a sensor 78 is arranged. The sensor 78 is provided for sensing a purity level QUAL of the paraffin that currently flows through the conduit 42. Thus, during pumping of the paraffin towards the retort 12 and back to the containers 70, 72, 74, the different purity levels QUAL of the currently used paraffin before and after the treatment of the tissue samples can be determined. The sensor 78 is, for example, an optical sensor which detects turbidity or coloration of the paraffin, wherein the paraffin may be treated with a dye for determining the purity level QUAL. Alternatively, the density or the conductance of the paraffin can be detected with the sensor 78, dependent on which the purity level QUAL can then be determined.

Figure 3:
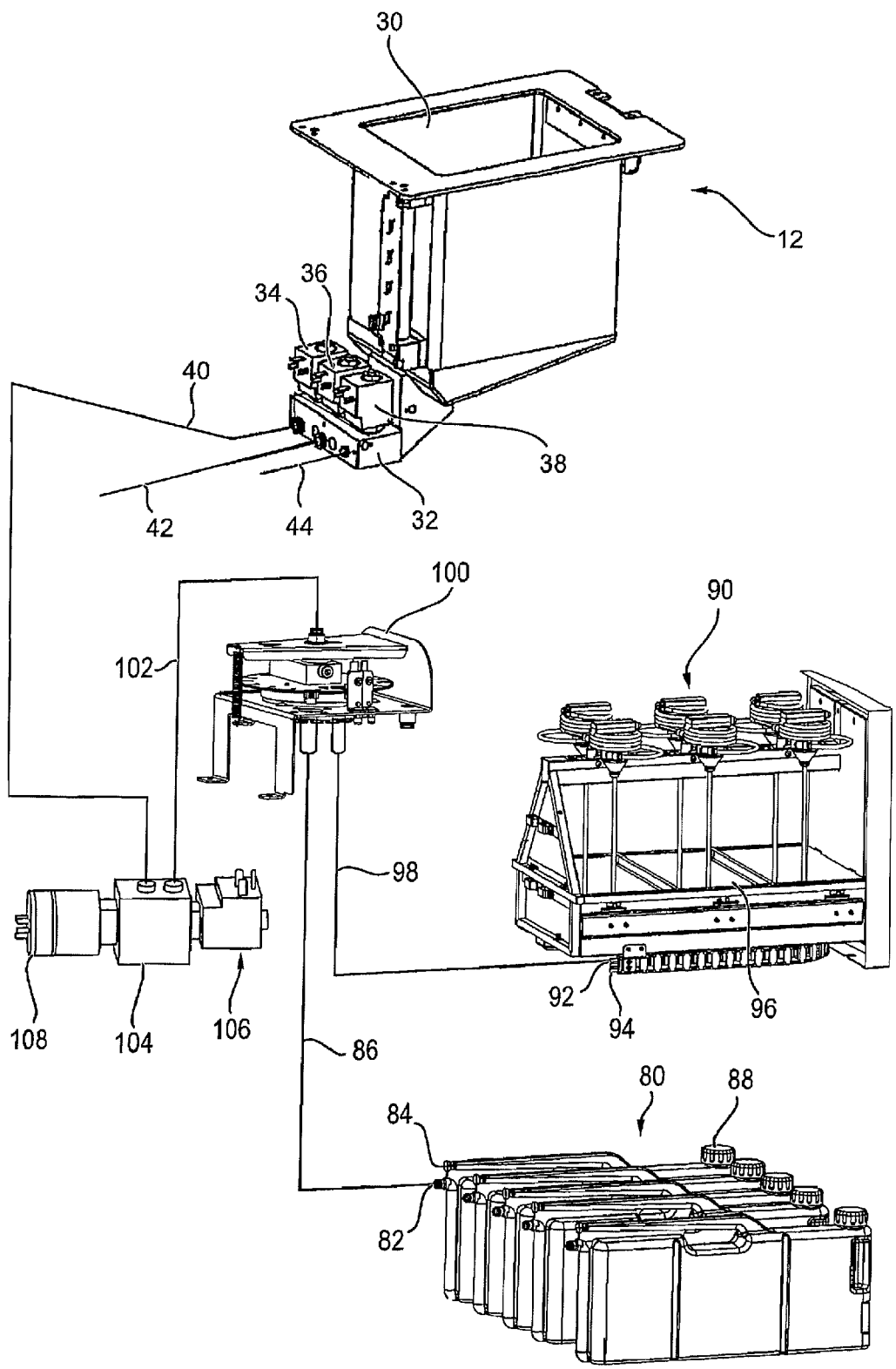
FIG. 3 shows various components of a tissue processor relating to dehydration, cleaning or an intermediate treatment of the tissue samples.

FIG. 3 shows system bottles 80 which each have a connection 82 for a conduit 86 for pumping out a process medium, and a connection 84 for applying pressure to the system bottles 80. Further, the system bottles 80 have caps 88 via which the process medium can be filled in.

In the system bottles 80, chemically basically the same process medium is contained, each of the various system bottles 80 containing the respective process medium with a different purity level QUAL. In this connection, the process media with different purity levels QUAL can also be referred to as different process media.

In stations 90 with different baths 96, further process reagents with different purity levels QUAL can be stored. The stations 90 each have one connection 92 for the transport of the respective process medium and one compressed air connection 94 for applying pressure to the stations. The connection 92 communicates with a rotational valve 100 via a conduit 98.

Depending on the operating position of the rotational valve 100, the conduit 86 or the conduit 98 communicates with the conduit 102 which leads from the rotational valve 100 to the coupling element 104. On the coupling element 104, a density sensor 106 and a pressure sensor 108 are arranged. The density sensor 106 and the pressure sensor 108 allow to detect the density of the process medium which currently flows through the coupling element 104. Depending on the density of the process medium, its purity level QUAL can be determined. Thus, the density sensor 106 and the pressure sensor 108 form a sensor module for detecting a measured value which is representative of the purity level QUAL of the process medium. The density sensor 106 is particularly suited for determining the purity level QUAL of alcohol or xylene.

The process media which are stored in the stations 90 or the system bottles 80 comprise, for example, fixation reagents, in particular alkaline fixation reagents, for example formalin, dehydrating reagents, in particular alcohols, in particular ethanol, intermedia, for example isopropanol or aromatic hydrocarbons, in particular xylene, and/or cleaning reagents, in particular distilled water. Further, the fixation reagents, the dehydrating reagents and/or the intermedia can also be used for cleaning, and in this connection also be referred to as cleaning reagents. As an alternative to the density sensor 106 and/or the pressure sensor, one or more other sensors can likewise be provided. What is important is that by means of the respective sensor the purity level QUAL of the respective process medium can be determined. Preferably, just as many sensors are provided that the purity levels QUAL of all process media used can be determined. The purity level QUAL can, for example, also be determined by means of a photo sensor, a conductance measurement and/or by means of a measurement of a pH value of the respective process medium.

The tissue samples are now successively subjected to the individual process steps and thus successively exposed to the different process media. In particular, the tissue samples are successively exposed to process media with different purity levels QUAL during the partial process steps. During the treatment with chemically identical process media having different purity levels QUAL, the tissue samples are exposed to the process media preferably with increasing purity level QUAL.

On a storage medium of a control device for the operation of the tissue processor, preferably a program is stored (FIG. 4). The program serves to automatically determine the purity level QUAL of the currently used process medium and to automatically decide on the further handling of the respective process medium.

The program is preferably started in a step S2, in which variables may be initialized.

In a step S4, a measured value MESS of the sensor or the sensors 78, 106 is detected.

In a step S6, the purity level QUAL is determined depending on the measured value MESS. For this purpose, a data base can, for example, be stored on the storage medium, in which the corresponding purity levels QUAL are assigned to the different measured values MESS.

In a step S8, it is checked whether the purity level QUAL is smaller than a predetermined threshold value THD. If the condition of step S8 is met, then the purity level QUAL is sufficiently good so that the process medium can still be used for the same process step and the program is preferably continued in a step S12. If the condition of step S8 is not met, then this is representative of the fact that the purity level QUAL has decreased such that the process medium can no longer be used for the same process step. Further, the program is then continued in a step S10.

In the step S10, a re-arrangement of the process media takes place. In particular, a process medium classified as a third process medium MED3 is subsequently classified as a second process medium MED2 and thus subsequently no longer used for a third one of the partial process steps but for a second one of the partial process steps. The current second process medium MED2 is subsequently classified as a first process medium MED1 and subsequently used for a first one of the partial process steps. The process medium currently classified as the first process medium MED1 is replaced by means of a renewal command NEW and is exchanged with a new process medium having the highest purity level QUAL, which is classified as the third process medium MED3 and used for the third partial process step. Thus, the contaminated process media are not always replaced by process media having the highest purity level QUAL but always by a process medium having the next higher purity level QUAL. In doing so, the process media are preferably not transferred by pumping but are merely classified differently.

In step S12, the program can be terminated. Preferably, however, the program is re-executed whenever the process medium is conducted from the container to the retort 12 or from the retort 12 back to the respective container.

The invention is not restricted to the embodiments described. For example, all process media can be conducted to the retort via merely one conduit or even more conduits can be present for the process media mentioned or for further process media. The number of the sensors provided is then reduced or increased accordingly. Further, the sensors can be arranged very close to the valve, the containers or the retort, for example, within the same housing.

LIST OF REFERENCE SIGNS 10 tissue processor
12 retort
13 cabinet
14 drawer
15 reagents 16 handle
17 drawer
18 table plate
20 working area
22 control device
24 screen
30 opening
32 valve arrangement
34, 36, 38 valves
40, 42, 44 conduits
46 distributor
48, 50, 52, 54 valves
56 conduit
58 supply station
60 pull-out rails
62 handle
64, 66, 68 conduits
70 first container
72 second container
74 third container
78 sensor
80 system bottles
82, 84 connections
86, 98 conduits
88 caps
90 stations
92, 94 connections
96 baths
100 rotational valve
102 conduit
104 coupling element
106 density sensor
108 pressure sensor
START program start
MESS measured value
QUAL purity level
THD threshold value
MED1 first process medium
MED2 second process medium
MED3 third process medium
END program end
S2 to S12 method steps

What is claimed is:

1. An apparatus for processing tissue samples, comprising:
at least one retort for accommodating tissue samples;
at least one container for storing alcohol or xylene;
a valve adapted to connect the at least one retort with the at least one container depending on an operating position of the valve; and
at least a first sensor that is arranged in flow direction between the container and the retort for measuring a value of a parameter that represents a purity level of the alcohol or xylene; wherein
the first sensor and the valve are configured to replace the alcohol or xylene depending on the value of the parameter that represents the purity level.

2. The apparatus according to claim 1, comprising two or more containers for accommodating one process medium each, wherein the valve is adapted to connect the at least one retort with the two or more containers depending on an operating position of the valve.

3. The apparatus according to claim 1, comprising a sensor module that includes the first sensor and at least a second sensor that is arranged in flow direction between the retort and the container.

4. The apparatus according to claim 2, comprising a sensor module that includes the first sensor and at least a second sensor that is arranged in flow direction between the retort and the two or more containers.

5. The apparatus according to claim 1, comprising a sensor module that includes the first sensor and at least a second sensor that is arranged in flow direction between the retort and the valve.

6. The apparatus according to claim 1, wherein the first sensor is at least one of a density sensor, a photo sensor and electric conductivity sensor.

7. The apparatus according to claim 1, comprising a sensor module that includes the first sensor and at least a second sensor wherein at least one of the first sensor and second sensor is at least one of a density sensor, a photo sensor and electric conductivity sensor.

8. A method for processing tissue samples with an apparatus, the apparatus comprising: at least one retort for accommodating tissue samples; at least one container for storing alcohol or xylene; a valve adapted to connect the at least one retort with the at least one container depending on an operating position of the valve; and at least a first sensor that is arranged in flow direction between the container and the retort for measuring a value of a parameter that represents a purity level of the alcohol or xylene; wherein the first sensor and the valve are configured to replace the alcohol or xylene depending on the value of the parameter that represents the purity level;
said method comprising:
conducting alcohol or xylene at least one of from the container into the retort and from the retort into the container;
automatically measuring by means of the sensor the value of the parameter that represents the purity level of the alcohol or xylene; and
replacing the alcohol or xylene depending on the value of the parameter that represents the purity level.

9. The method according to claim 8, comprising:
checking whether the purity level is smaller than a predetermined threshold value; and
automatically deciding depending on a result of said checking for which process step the process medium is used.

10. The method according to claim 8, comprising:
checking whether the purity level is smaller than a predetermined threshold value; and
automatically deciding depending on a result of said checking whether the process medium is to be replaced.

* * * * *